United States Patent [19]

Baltrüschat et al.

[11] Patent Number: 4,615,727

[45] Date of Patent: Oct. 7, 1986

[54] CYCLOALKYL AMINO-S-TRIAZINES AND THEIR USE AS SELECTIVE AGENTS AGAINST WEEDS AND NOXIOUS GRASSES

[75] Inventors: Helmüt Baltrüschat, Nottuln-Darup; Horst Schnurbusch, Herne, both of Fed. Rep. of Germany

[73] Assignee: Chemische Werke Huls Aktiengesellschaft, Marl, Fed. Rep. of Germany

[21] Appl. No.: 500,381

[22] Filed: Jun. 2, 1983

[30] Foreign Application Priority Data

Jun. 11, 1982 [DE] Fed. Rep. of Germany ....... 3222147

[51] Int. Cl.[4] .................... C07D 251/52; A01N 43/70
[52] U.S. Cl. ......................................... 71/93; 544/208
[58] Field of Search ............................ 544/208; 71/93

[56] References Cited

U.S. PATENT DOCUMENTS

| | | | |
|---|---|---|---|
| 3,629,256 | 12/1971 | Berrer et al. | 544/208 |
| 3,714,162 | 1/1973 | Chupp | 71/93 |
| 3,766,182 | 10/1973 | Kuhne et al. | 544/208 |
| 3,786,053 | 1/1974 | Chapman et al. | 544/208 |
| 4,007,032 | 2/1977 | Berrer | 544/208 |

OTHER PUBLICATIONS

Kuehne et al., Chemical Abstract, vol. 77, entry 19682k (1972).
Kuehne et al., Chemical Abstracts, vol. 80, entry 70847g (1974).
Chapman et al., Chemical Abstracts, vol. 80, entry 83069e (1974).
Schwarze et al., Chemical Abstracts, vol. 77, entry 34593a (1972).
Kralovic et al., Chemical Abstracts, vol. 90, entry 147025d (1979).

*Primary Examiner*—John M. Ford
*Attorney, Agent, or Firm*—Oblon, Fisher, Spivak, McClelland & Maier

[57] ABSTRACT

A herbicidal compound, and a method of use therefor, for the selective treatment of useful plant cultures, having a broad spectrum of activity against weeds and noxious grasses in pre-emergence and/or post-emergence periods having the formula:

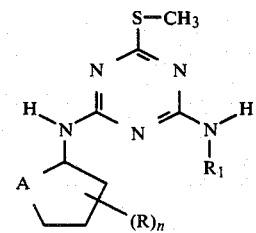

wherein $R_1$ is a straight-chain or branched-chain alkyl, alkoxy, alkoxyalkyl, or alkylol radical having less than a total of 15 oxygen and carbon atoms combined, or a hydrogen atom; (R) is a lower alkyl group; A is —$CH_2$— or —$CH_2CH_2$—; with the proviso that n is 0–6, when A is —$CH_2$—, and n is 3–6, when A is —$CH_2CH_2$—; and wherein the substituents (R) on the cycloalkyl ring are identical to or different from each other.

9 Claims, No Drawings

CYCLOALKYL AMINO-S-TRIAZINES AND THEIR USE AS SELECTIVE AGENTS AGAINST WEEDS AND NOXIOUS GRASSES

BACKGROUND OF THE INVENTION

1. Field of the Invention

This invention relates to certain cycloalkyl amino-s-triazines and a process for using these compounds as selective agents against weeds and noxious grasses.

2. Description of the Prior Art

Numerous derivatives of the 6-methylthio-s-triazines are known wherein the 2- and 4-positions on the triazine ring are substituted by alkyl amines. For example, the following such derivatives are known: Desmetryn(2-methylamino-4-isopropyl amino), Simetryn(2,4-bis-ethylamino), Ametryn(2-ethyl amino-4-isopropyl amino), Prometryn(2,4-bis-isopropyl amino), Methoprotryn(2-isopropyl amino-4(3-methoxypropyl amino)), MPMT(2,4-bis-(3-methoxypropyl amino)) and, Terbutryn(2-ethyl amino-4-tert.butyl amino). Terbutryn is probably the best-known compound of this series.

Additionally, from the 6-ethylthio derivatives, Dipropetryn(2,4-bis-isopropyl amino) is also known. See R. Wegler, "Chemie der Pflanzenschutz-und Schädlingsbekampfungsmittel" (Chemistry of Plant Protection and Pest Control Agents), Springer Verlag: Berlin, Heidelberg, New York; Vol. 2, (1970, pp. 372–374) and Vol. 5 (1977, pp. 346–50).

Most of these compounds may be used as soil and leaf herbicides against mono- and dicotyledons in the pre- and/or post-emergence periods. For example, Terbutryn is selective in winter grains, but is not always sufficiently effective against noxious grasses like slender foxtail and corn grass. Usually, good herbicidal qualities are also found in other 6-methylthio-1,3,5-triazines having substituents from the lower alkyl-substituted amine group, however, it is not always desirable to have the limitation of selective herbicidal action.

JA-OS No. 47 23 436 describes the 2-cyclohexyl amino derivatives of 6-methylthio-s-triazine, 6-propylthio-s-triazine, and 6-butylthio-s-triazine. These substances are described as having an unsatisfactory degree of selectivity between useful plants and noxious plants.

Therefore, a need continues to exist for herbicidal compounds which exhibit a broad spectrum of activity against noxious grasses and dicotyledonous weeds, both in pre-emergence and post-emergence application, without causing damage to cultivated plants.

SUMMARY OF THE INVENTION

Accordingly, it is an object of this invention to provide a herbicidal compound which exhibits a broad spectrum of activity against noxious grasses and dicotyledonious weeds.

It is also an object of the present invention to provide a herbicidal compound with a high degree of selectivity, which exhibits a broad spectrum of activity against noxious grasses and dicotyledonous weeds, both in pre-emergence and post-emergence application, without causing damage to cultivated plants.

Moreover, it is also an object of this invention to provide a herbicidal composition and a method for using the same in the control of noxious grasses and weeds.

According to the present invention, the foregoing and other objects are attained by providing a herbicidal compound for the selective treatment of useful plant cultures with a broad spectrum of activity against noxious grasses and weeds before and/or after sprouting of the seed, having the formula:

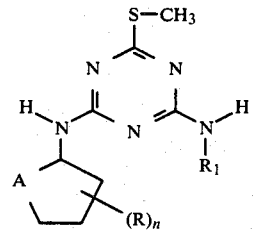

wherein $R_1$ is a straight-chain or branched-chain alkyl, alkoxy, alkoxyalkyl or alkylol radical having less than a combined total of 15 carbon and oxygen atoms, or a hydrogen atom; (R) is a lower alkyl radical; A is $-CH_2-$ or $-CH_2-CH_2-$; and n is 0–6, when A is $-CH_2-$, and n is 3–6, when A is $-CH_2-CH_2-$, whereby the substituents R on the cycloalkyl ring are identical to or different from each other.

DETAILED DESCRIPTION OF THE PREFERRED EMBODIMENTS

According to the present invention, a herbicidal compound having the formula:

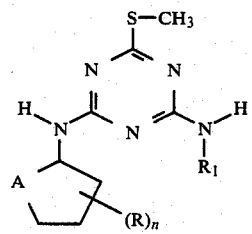

wherein $R_1$ is a straight-chain or branched-chain alkyl, alkoxy, alkoxyalkyl or alkylol radical having less than a combined total of 15 carbon and oxygen atoms, or a hydrogen atom; (R) is a lower alkyl radical; A is $-CH_2-$ or $-CH_2-CH_2-$; and n is 0–6 when A is $-CH_2-$, and n is 3–6 when A is $-CH_2-CH_2-$, whereby the substituents R on the cycloalkyl ring are identical to or different from each other, exhibits a broad spectrum of activity against noxious grasses and dicotyledonous weeds, both in pre-emergence and post-emergence application. However, the compounds of the formula I also display a wide range of selectivity against numerous cultivated plants, and cause no damage thereto when used in the presence of the cultivated plants.

It has been surprisingly discovered that in the alkylthio-s-triazines, the compounds which are substituted with a lower straight-chain or lower branched-chain alkylamine and an unsubstituted or alkyl-substituted cycloaliphatic amine exhibit an action against noxious grasses which is superior compared to that of the previously known compounds. The compounds of this invention also may also be seen to be effective as selective weed control agents.

The herbicidal compounds of the formula I may be used individually. However, the herbicidal compounds of the present invention may also be used in combination. For example, herbicidal compounds having different $R_1$ or (R) substituents, different groups for A, or different values of n, or even (R) substituents being substituted, may be used in combination with each other.

The herbicidal compounds of the present invention may also be mixed, individually or in combination, with other herbicides, fungicides or growth regulators, and applied to particular cultivated plants. It is also possible to mix the herbicidal compounds with mineral fertilizers. This is most easily performed with fertilizer solutions.

Auxiliary agents such as carrier agents, diluting agents, solvents, wetting agents, adhesion agents and dispersing and/or emulsifying agents are usually added to the active substances of this invention prior to application. The addition of these auxiliary agents improves the spraying and facilitates an even distribution of the active herbicidal compounds of this invention.

The herbicidal compounds of formula I exhibit a broad spectrum of activity against noxious grasses and dicotyledonous weeds, both in pre-emergence and/or post-emergence application, while also displaying a wide range of selectivity against numerous cultivated plants. The herbicidal compounds of this invention are selective in the pre-emergence application and/or the post-emergence application in soybeans (17), cotton (4), rice (15), barley (8), and wheat (22), for example. See Table 2.

In addition, the present compounds exhibit a broad spectrum of activity against noxious grasses, such as slender foxtail (1), corn grass (24), wild oats (6), and panic grass types, Echinocloa spp., Digitaris spp., Setaria spp., (cf. 10). Further, the present compounds also exhibit a broad spectrum of activity against dicotyledonous weeds, such as chickweed (20), goosegrass (13), camomile (11), white goosefoot (21), field mustard (2), dead nettle (18), amaranth (3), corn poppy (12), redshank (5) and field scabious (7).

The herbicidal compounds of this invention may be applied to plant cultures in an amount ranging from 0.125 to 10 kg/ha. However, these compounds are preferably applied in an amount ranging from 0.5 to 2.5 kg/ha. The present compounds have a satisfactory herbicidal activity from at least 0.25 kg/ha, calculated for the pure active herbicidal, and may be used in the plant cultures listed above without damage to the cultivated plants, despite their broad range of activity.

The use of the compounds of the invention is not limited to the plant cultures or types listed above, but may also be applied to other plants. Depending on their concentration, the present herbicidal compounds may also be used for total weed control, e.g., in industrial parks, on track systems or on paths with or without trees.

Moreover, the herbicidal compounds of this invention are also suitable for use in weed control in permanent cultures such as, cultures of forest trees, decorative wood, fruit, wine, citrus fruit, nuts, bananas, coffee, tea, rubber, oil palms, cocoa trees, berries and hops.

In some plant types, several of the herbicidal compounds of the present invention inhibit the plant height without reducing the yield. Therefore, they may be also be employed as growth regulators. Also, several of the new compounds may also be used as defoliants, dessicants, weed killers and germination inhibitors.

The compounds of formula I may be produced according to known methods by reacting cyanuric chloride, preferably in a solvent or a solvent mixture such as acetone, acetone-water, dioxane, dioxane-water, tetrahydrofuran or dimethylformamide, with the corresponding amines at a temperature appropriate for each instance. The temperature is generally in the range of $-30°$ C. to $50°$ C.

Additionally, known methods may be used for selective substitution on the 1,3,5-triazine ring. Also, the chlorine derivatives obtained, initially, may be reacted with sodium thiomethylate in isopropanol or other solvents to produce the corresponding methylthio-s-1,3,5-triazine derivative.

The present invention will be further illustrated by certain examples and references which are provided for purposes of illustration only and are not intended to limit the present invention.

EXAMPLE 1

Preparation of 2-cyclopentyl amino-4-amino-6-methylthio-s-triazine 184.5 g (1.00 mole) of cyanuric chloride is dissolved in 900 ml acetone and added drop-by-drop with strong agitation during a period of 30 minutes into 1100 ml water of $0°-2°$ C. 85.0 g (1.00 mole) of cyclopentyl amine is then added drop-by-drop, also under strong agitation, into the suspension obtained during the 30 minute period, at $0°-2°$ C. The batch is then agitated for 30 minutes, whereby the suspended product goes almost completely into solution.

In order to neutralize the HCl released by the reaction, 40.0 g (1.00 mole) of NaOH is subsequently added drop-by-drop as a 30% solution during a period of 30 minutes. In general, a pH of 8.0 is not exceeded in the first 20-25 minutes. A pH of 8.5-9.0 is not reached until near the end of neutralization.

The batch is strongly agitated and the temperature is held at $0°-2°$ C. During the addition of the NaOH the dichloro-cyclopentyl amine-s-triazine precipitates in a fine distribution. It is then present as a suspension which can be well agitated.

70.0 g (1.03 mole) of 25% $NH_4OH$ is then added with agitation at $5°$ C. The batch is heated to $30°-35°$ C. and agitated for 4 hours. The following neutralization of the HCl released with 1.00 mole of 30% NaOH requires 8 hours longer.

The acetone is then removed by distillation, whereby the 2-chloro-4-cyclopentyl amino-6-amino-s-triazine precipitates as a soft granular product and is isolated by filtration.

For the further reaction, 213.5 g (1.00 mole) of the preceding product triazine is reacted with 336 g (1.20 mole) of a 25% aqueous $NaSCH_3$ solution and 350 ml isopropanol and agitated for 15 hours at $82°-83°$ C. The product remains clearly dissolved, and an aqueous layer separates from the organic phase.

For work-up, the isopropyl alcohol is removed by distillation and the precipitated yellow resin-like product is washed three times with hot water at $80°$ C. After drying in a vacuum at $80°$ C., a yield of 70% of 2-cyclopentylamino-4-amino-6-methylthio-s-triazine is afforded, based on the amount of cyanuric chloride use.

EXAMPLE 2

Preparation of 2-cyclopentyl amino-4-methyl amino-6-methylthio-s-triazine

2-Cyclopentyl amino-4,6-dichloro-s-triazine is produced in the same manner as described in Example 1.

31.9 g (1.03 mole) of methyl amine is then added drop-by-drop with agitation during a period of 45 minutes at 0°–5° C. as a 30% aqueous solution and agitated for 2 hours, whereby the temperature slowly rises to 30°–35° C. The agitation is then continued 4 more times at 30°–35° C. The subsequent neutralization with 1.00 mole 30% NaOH lasts approximately 4 hours.

In order to separate the 2-chloro-4-cyclopentyl amino-6-methyl amino-2-triazine, the acetone is removed by distillation and the precipitated white product is suction-filtered.

227.5 g (1.00 mole) of the intermediate product triazine is then reacted with a 25% aqueous NaSCH$_3$ solution in the same manner as in Example 1.

After drying in a vacuum at 80° C., the yield of 2-cyclopentyl amino-4-methyl amino-6-methylthio-2-triazine is 75% based on the amount of cyanuric chloride used.

Other cycloalkyl amino-2-triazines of the invention can be produced in an analogous manner. A selection of them, including Examples 1 and 2, is given in Table 1a.

In Examples 15 to 26 TMCP=2,2,4- or 2,4,4-trimethyl cyclopentyl,

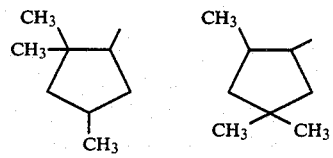

and in Examples 27 to 36 TMC=3,3,5-trimethyl cyclohexyl

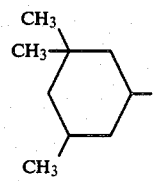

(There are stable cis and trans forms and (cis-trans) mixtures in this group).

Table 1b gives the meaning of R$_1$, A and n as well as the position on the ring occupied by the n substituents R (=CH$_3$) for these 36 compounds with reference to formula I, as well as their melting points.

TABLE 1a

List of the methylthio cycloalkyl-s-triazines produced

| Example | |
|---|---|
| 1 | 2-Cyclopentyl amino-4-amino-6-methylthio-s-triazine |
| 2 | 2-Cyclopentyl amino-4-methyl amino-6-methylthio-s-triazine |
| 3 | 2-Cyclopentyl amino-4-ethyl amino-6-methylthio-s-triazine |
| 4 | 2-Cyclopentyl amino-6-methylthio-s-triazine |
| 5 | 2-Cyclopentyl amino-4-propyl amino-6-methylthio-s-triazine |
| 6 | 2-Cyclopentyl amino-4-tert.-butyl amino-6-methylthio-s-triazine |
| 7 | 2-Cyclopentyl amino-4-2'hydroxyethyl amino-6-methylthio-s-triazine |
| 8 | 2-Cyclopentyl amino-4-3'methoxy-propyl amino-6-methylthio-s-triazine |
| 9 | 2-Cyclopentyl amino-4-3'ethoxy-propyl amino-6-methylthio-s-triazine |
| 10 | 2-Cyclopentyl amino-4-2'methoxy-ethyl amino-6-methylthio-s-triazine |
| 11 | 2-Cyclopentyl amino-4-3'butoxy-propyl amino-6-methylthio-s-triazine |
| 12 | 2-Cyclopentyl amino-4-3'hexoxy-propyl amino-6-methylthio-s-triazine |
| 13 | 2-Cyclopentyl amino-4-3'isopropoxy-propyl amino-6-methylthio-s-triazine |
| 14 | 2-Cyclopentyl amino-4-3'sec.-butoxy-propyl amino-6-methylthio-s-triazine |
| 15 | 2-TMCPamino-4-amino-6-methylthio-s-triazine |
| 16 | 2-TMCPamino-4-methyl amino-6-methylthio-s-triazine |
| 17 | 2-TMCPamino-4-ethyl amino-6-methylthio-s-triazine |
| 18 | 2-TMCPamino-4-isopropyl amino-6-methylthio-s-triazine |
| 19 | 2-TMCPamino-4-propyl amino-6-methylthio-s-triazine |
| 20 | 2-TMCPamino-4-tert. butyl amino-6-methylthio-s-triazine |
| 21 | 2-TMCPamino-4-2'methoxy-ethyl amino-6-methylthio-s-triazine |
| 22 | 2-TMCPamino-4-3'methoxy-propyl amino-6-methylthio-s-triazine |
| 23 | 2-TMCPamino-4-3'ethoxy-propyl amino-6-methylthio-s-triazine |
| 24 | 2-TMCPamino-4-3'butoxy-propyl amino-6-methylthio-s-triazine |
| 25 | 2-TMCPamino-4-3'hexoxy-propyl amino-6-methylthio-s-triazine |
| 26 | 2-TMCPamino-4-3' isopropoxy-propyl amino-6-methylthio-s-triazine |
| 27 | 2-TMCamino-4-amino-6-methylthio-s-triazine |
| 28 | 2-TMCamino-4-methyl amino-6-methylthio-s-triazine |
| 29 | 2-TMCamino-4-ethyl amino-6-methylthio-s-triazine |
| 30 | 2-TMCamino-4-isopropyl amino-6-methylthio-s-triazine |
| 31 | 2-TMCamino-4-propyl amino-6-methylthio-s-triazine |
| 32 | 2-TMCamino-4-tert.-butyl amino-6-methylthio-s-triazine |
| 33 | 2-TMCamino-4-2'methoxy-ethyl amino-6-methylthio-s-triazine |
| 34 | 2-TMCamino-4-3'methoxy-propyl amino-6-methylthio-s-triazine |
| 35 | 2-TMCamino-4-3'ethoxy-propyl amino-6-methylthio-s-triazine |
| 36 | 2-TMCamino-4-3'butoxy-propyl amino-6-methylthio-s-triazine |

TABLE 1b

Compounds produced and their various substituents according to formula I and their melting ranges

| Example | R$_1$ | A | n | position of (R)$_n$ | melting range °C. |
|---|---|---|---|---|---|
| 1 | —H | —CH$_2$— | 0 | — | 65–73 |
| 2 | —CH$_3$ | —CH$_2$— | 0 | — | 90–95 |
| 3 | —CH$_2$—CH$_3$ | —CH$_2$— | 0 | — | 83–88 |
| 4 | —CH=(CH$_3$)$_2$ | —CH$_2$— | 0 | — | 120–123 |
| 5 | —CH$_2$—CH$_2$—CH$_3$ | —CH$_2$— | 0 | — | 76–82 |
| 6 | —C(CH$_3$)$_3$ | —CH$_2$— | 0 | — | 105–110 |
| 7 | —CH$_2$—CH$_2$OH | —CH$_2$— | 0 | — | 35–45 |
| 8 | —CH$_2$—CH$_2$—CH$_2$—OCH$_3$ | —CH$_2$— | 0 | — | 65–70 |
| 9 | —CH$_2$—CH$_2$—CH$_2$—OCH$_2$—CH$_3$ | —CH$_2$— | 0 | — | 60–66 |

TABLE 1b-continued

Compounds produced and their various substituents according to formula I and their melting ranges

| Example | R$_1$ | A | n | position of (R)$_n$ | melting range °C. |
|---|---|---|---|---|---|
| 10 | —CH$_2$—CH$_2$—OCH$_3$ | —CH$_2$— | 0 | — | 85–97 |
| 11 | —CH$_2$—CH$_2$—CH$_2$—OCH$_2$—CH$_2$—CH$_2$—CH$_3$ | —CH$_2$— | 0 | — | 20–28 |
| 12 | —CH$_2$—CH$_2$—CH$_2$—OCH$_2$—CH$_2$—CH$_2$—CH$_2$—CH$_2$—CH$_3$ | —CH$_2$— | 0 | — | 20–30 |
| 13 | —CH$_2$—CH$_2$—CH$_2$—O—CH=C(CH$_3$)$_2$ | —CH$_2$— | 0 | — | 25–30 |
| 14 | —CH$_2$—CH$_2$—CH$_2$—O—CH$_2$—CH=(CH$_3$)$_2$ | —CH$_2$— | 0 | — | 25–32 |
| 15 | —H | —CH$_2$— | 3 | 2,2,4(2,4,4) | 50–57 |
| 16 | —CH$_3$— | —CH$_2$— | 3 | 2,2,4(2,4,4) | 52–63 |
| 17 | —CH$_2$—CH$_3$ | —CH$_2$— | 3 | 2,2,4(2,4,4) | 54–60 |
| 18 | —CH=(CH$_3$)$_2$ | —CH$_2$— | 3 | 2,2,4(2,4,4) | 30–38 |
| 19 | —CH$_2$—CH$_2$—CH$_3$ | —CH$_2$— | 3 | 2,2,4(2,4,4) | 48–54 |
| 20 | —C(CH$_3$)$_3$ | —CH$_2$— | 3 | 2,2,4(2,4,4) | 28–34 |
| 21 | —CH$_2$—CH$_2$—OCH$_3$ | —CH$_2$— | 3 | 2,2,4(2,4,4) | 30–40 |
| 22 | —CH$_2$—CH$_2$—CH$_2$OCH$_3$ | —CH$_2$— | 3 | 2,2,4(2,4,4) | 42–46 |
| 23 | —CH$_2$—CH$_2$—CH$_2$—OCH$_2$—CH$_3$ | —CH$_2$— | 3 | 2,2,4(2,4,4) | 34–38 |
| 24 | —CH$_2$—CH$_2$—CH$_2$—OCH$_2$—CH$_2$—CH$_2$—CH$_3$ | —CH$_2$— | 3 | 2,2,4(2,4,4) | 30–35 |
| 25 | —CH$_2$—CH$_2$—CH$_2$—OCH$_2$—CH$_2$—CH$_2$—CH$_2$—CH$_2$—CH$_3$ | —CH$_2$— | 3 | 2,2,4(2,4,4) | 26–32 |
| 26 | —CH$_2$—CH$_2$—CH$_2$—O—CH=(CH$_3$)$_2$ | —CH$_2$— | 3 | 2,2,4(2,4,4) | 25–30 |
| 27 | —H | —CH$_2$—CH$_2$— | 3 | 3,3,5 (cis-trans mixture) | 55–60 |
| 28 | —CH$_3$ | —CH$_2$—CH$_2$— | 3 | 3,3,5 (cis-trans mixture) | 55–62 |
| 29 | —CH$_2$—CH$_3$ | —CH$_2$—CH$_2$— | 3 | 3,3,5 (cis-trans mixture) | 53–58 |
| 30 | —CH=(CH$_3$)$_2$ | —CH$_2$—CH$_2$— | 3 | 3,3,5 (cis-trans mixture) | 50–54 |
| 31 | —CH$_2$—CH$_2$—CH$_3$ | —CH$_2$—CH$_2$— | 3 | 3,3,5 (cis-trans mixture) | 38–44 |
| 32 | —C=(CH$_3$)$_3$ | —CH$_2$—CH$_2$— | 3 | 3,3,5 (cis-trans mixture) | 42–46 |
| 33 | —CH$_2$—CH$_2$—O—CH$_3$ | —CH$_2$—CH$_2$— | 3 | 3,3,5 (cis-trans mixture) | 44–53 |
| 34 | —CH$_2$—CH$_2$—CH$_2$—O—CH$_3$ | —CH$_2$—CH$_2$— | 3 | 3,3,5 (cis-trans mixture) | 43–48 |
| 35 | —CH$_2$—CH$_2$—CH$_2$—O—CH$_2$—CH$_3$ | —CH$_2$—CH$_2$— | 3 | 3,3,5 (cis-trans mixture) | 40–45 |
| 36 | —CH$_2$—CH$_2$—CH$_2$—O—CH$_2$—CH$_2$—CH$_2$—CH$_3$ | —CH$_2$—CH$_2$— | 3 | 3,3,5 (cis-trans mixture) | 26–32 |

TABLE 2

Botanical Names of the Test Plants

| English designation | Latin designation |
|---|---|
| 1. slender foxtail | *Alopecurus myosuroides* |
| 2. field mustard | *Sinapis alba* |
| 3. amaranth | *Amaranthus retroflexus* |
| 4. cotton | *Gossypium hirsutum* |
| 5. redshank | *Polygonum persicaria* |
| 6. wild oats | *Avena fatua* |
| 7. field scabious | *Galinsoga parviflora* |
| 8. barley | *Hordeum vulgare* |
| 9. oats | *Avena sativa* |
| 10. barnyard grass | *Echinocloa crus-galli* |
| 11. camomile | *Matricaria maritima* |
| 12. corn poppy | *Papaver rhoeas* |
| 13. goose-grass | *Galium aparine* |
| 14. corn | *Zea mays* |
| 15. rice | *Oryza sativa* |
| 16. corn marigold | *Chrysanthenum segetum* |
| 17. soybean | *Glycine max* |
| 18. dead nettle | *Lamium purpureum* |
| 19. tomato | *Lycopersicum esculentum* |
| 20. chickweed | *Stellaria media* |
| 21. white goosefoot | *Chenopodium alba* |
| 22. wheat | *Triticum aestivum* |
| 23. vetch | *Vicia angustifolia* |
| 24. corn grass | *Apera spica-venti* |
| 25. winter rape-seed | *Brassica napa* |
| 26. sugar beet | *Beta vulgaris* |

EXAMPLE 3

Biological Testing of the Active Substances

A. Greenhouse Test Series with 4 kg/ha

Greenhouse tests were performed with the customary selection of useful and noxious plants in the pre-emergence and the post-emergence periods for all compounds of Table 1a (and 1b) with an application amount of 4 kg/ha. In general, a good activity against weeds and noxious grasses as well as no or only slight activity against useful plants was observed.

B. Greenhouse Test Series with 4, 3, 2 and 1 kg/ha

The greenhouse tests were repreated for a selection of the compounds of the invention which were determined to be the most effective in the first test series with an application amount of 4, 3, 2 and 1 kg/ha in reference to pure active substance and are collected in Tables 3a and b.

The amounts of active substance required in each instance were suspended in 1000 l water/ha.

In the pre-emergence period the compound was applied to the surface before the sprouting of the seed and in the post-emergence period it was applied to the leaf surface in the second to third leaf stage.

Three weeks after application a very good activity against dicotyledonous and monocotyledonous plants both in the pre-emergence and in the post-emergence periods (Tables 3a and 3b) was observed for the compounds of the invention.

The test results were evaluated with the customary grading, in which

1 = total activity = killing of the plants and

5 = no activity = plants as if untreated.

The compounds of the invention exhibit a superior activity against noxious grasses (e.g., slender foxtail, panic grass types, corn grass) and dicotyledonous weeds both in the pre-emergence and in the post-emergence periods (Tables 3a and 3b). In addition to this broad spectrum of activity the extraordinarily good compatability in grain cultures (such as barley, wheat), emergence period, which is surprising for triazine compounds, is remarkable and is not exhibited by the comparison compounds.

TABLE 3a

Herbicidal action of the compounds of the invention in application amounts of 4, 3, 2 and 1 kg active substance/ha. Application before the sprouting of the plants

| Test Plants kg/ha | Example 1 | | | | Example 2 | | | | Example 3 | | | | Example 4 | | | | Example 8 | | | | Example 9 | | | | Example 17 | | | |
|---|---|---|---|---|---|---|---|---|---|---|---|---|---|---|---|---|---|---|---|---|---|---|---|---|---|---|---|---|
| | 4 | 3 | 2 | 1 | 4 | 3 | 2 | 1 | 4 | 3 | 2 | 1 | 4 | 3 | 2 | 1 | 4 | 3 | 2 | 1 | 4 | 3 | 2 | 1 | 4 | 3 | 2 | 1 |
| (part 1) | | | | | | | | | | | | | | | | | | | | | | | | | | | | |
| field mustard | 4 | 5 | 5 | 5 | 1 | 3 | 4 | 5 | 1 | 3 | 4 | 4 | 5 | 5 | 5 | 1 | 1 | 1 | 4 | 4 | 4 | 5 | 5 | 3 | 3 | 5 | 5 | |
| tomato | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 |
| barnyard grass | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 |
| oats | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 |
| wild oats | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 |
| slender foxtail | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 |
| chickweed | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 |
| goose-grass | 1 | 1 | 2 | 3 | 1 | 1 | 2 | 3 | 1 | 1 | 2 | 2 | 4 | 4 | 4 | 5 | 4 | 4 | 4 | 5 | 4 | 4 | 4 | 5 | 3 | 4 | 4 | 5 |
| camomile | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 |
| white goosefoot | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 |
| corn grass | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 |
| barley | 4 | 4 | 5 | 5 | 4 | 5 | 5 | 5 | 4 | 5 | 5 | 5 | 4 | 5 | 5 | 4 | 4 | 5 | 5 | 4 | 4 | 5 | 5 | 3 | 4 | 5 | 5 | |
| wheat | 4 | 4 | 5 | 5 | 4 | 5 | 5 | 5 | 4 | 5 | 5 | 5 | 4 | 5 | 5 | 4 | 4 | 5 | 5 | 4 | 4 | 4 | 5 | 3 | 4 | 5 | 5 | |
| (part 2) | | | | | | | | | | | | | | | | | | | | | | | | | | | | |
| dead nettle | 1 | 1 | 1 | 1 | 1 | 1 | 1 | 1 | 1 | 1 | 1 | 1 | 1 | 1 | 1 | 1 | 1 | 1 | 4 | 1 | 1 | 3 | 4 | 1 | 1 | 2 | 4 | |
| amaranth | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 3 | |
| winter rape-seed | 1 | 1 | 4 | 4 | 2 | 2 | 4 | 4 | 1 | 1 | 2 | 5 | 1 | 1 | 1 | 1 | 1 | 1 | 1 | 2 | 2 | 2 | 2 | 2 | 4 | 4 | 4 | 5 |
| redshank | 1 | 1 | 1 | 1 | 1 | 1 | 1 | 1 | 1 | 1 | 1 | 1 | 1 | 1 | 1 | 2 | 1 | 1 | 1 | 1 | 1 | 1 | 1 | 1 | 1 | 1 | 1 | 3 |
| corn poppy | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 |
| bristle grass | 1 | 1 | 1 | 1 | 1 | 1 | 1 | 1 | 1 | 1 | 1 | 1 | 1 | 1 | 1 | 4 | 1 | 1 | 1 | 1 | 1 | 1 | 1 | 1 | 1 | 1 | 1 | 2 |
| finger grass | 1 | 1 | 1 | 1 | 1 | 1 | 1 | 1 | 1 | 1 | 1 | 1 | 1 | 1 | 1 | 3 | 1 | 1 | 1 | 1 | 1 | 1 | 1 | 1 | 1 | 1 | 1 | 1 |
| sesbania spp. | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 |
| ipomoea spp. | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 3 |
| soybean | 3 | 3 | 3 | 5 | 3 | 3 | 4 | 4 | 4 | 4 | 4 | 5 | 4 | 5 | 5 | 5 | 4 | 4 | 4 | 5 | 4 | 5 | 5 | 5 | 5 | 5 | 5 | 5 |
| cotton | 5 | 5 | 5 | 5 | 5 | 5 | 5 | 5 | 4 | 5 | 5 | 5 | 5 | 5 | 5 | 5 | 4 | 4 | 5 | 5 | 4 | 4 | 5 | 5 | 5 | 5 | 5 | 5 |
| rice | 5 | 5 | 5 | 5 | 4 | 4 | 4 | 4 | 5 | 5 | 5 | 5 | 5 | 5 | 5 | 5 | 5 | 5 | 5 | 5 | 5 | 5 | 5 | 5 | 5 | 5 | 5 | 5 |
| corn | 3 | 3 | 4 | 4 | 3 | 4 | 4 | 4 | 3 | 4 | 4 | 5 | 4 | 4 | 4 | 4 | 3 | 3 | 4 | 5 | 3 | 3 | 4 | 4 | 4 | 4 | 5 | 5 | soybeans, cotton and rice, among others, in the pre-

TABLE 3b

Herbicidal action of the compounds of the invention in application amounts of 4, 3, 2 and 1 kg active substance/ha. Application after the sprouting of the plants

| Test Plants kg/ha | Example 1 | | | | Example 2 | | | | Example 3 | | | | Example 4 | | | | Example 8 | | | | Example 9 | | | | Example 17 | | | |
|---|---|---|---|---|---|---|---|---|---|---|---|---|---|---|---|---|---|---|---|---|---|---|---|---|---|---|---|---|
| | 4 | 3 | 2 | 1 | 4 | 3 | 2 | 1 | 4 | 3 | 2 | 1 | 4 | 3 | 2 | 1 | 4 | 3 | 2 | 1 | 4 | 3 | 2 | 1 | 4 | 3 | 2 | 1 |
| (part 1) | | | | | | | | | | | | | | | | | | | | | | | | | | | | |
| field mustard | 1 | 1 | 1 | 3 | 1 | 2 | 2 | 4 | 1 | 1 | 1 | 1 | 1 | 1 | 1 | 2 | 1 | 1 | 1 | 1 | 1 | 1 | 1 | 1 | 1 | 1 | 1 | 1 |
| tomato | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 |
| barnyard grass | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 |
| oats | 1 | 1 | 1 | 1 | 1 | 1 | 1 | 1 | 1 | 1 | 1 | 1 | 1 | 1 | 3 | 3 | 1 | 1 | 1 | 1 | 1 | 1 | 1 | 1 | 1 | 1 | 1 | 1 |
| wild oats | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 |
| slender foxtail | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 |
| chickweed | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 |
| goose-grass | 1 | 1 | 1 | 2 | 1 | 1 | 2 | 3 | 1 | 1 | 1 | 2 | 5 | 5 | 5 | 5 | 1 | 1 | 2 | 4 | 1 | 1 | 3 | 3 | 1 | 1 | 3 | 3 |
| camomile | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 |
| white goosefoot | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 |
| corn grass | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 |
| barley | 1 | 1 | 1 | 1 | 1 | 1 | 3 | 1 | 1 | 2 | 2 | 1 | 1 | 2 | 2 | 1 | 1 | 1 | 1 | 1 | 1 | 1 | 1 | 1 | 1 | 1 | 1 | 1 |
| wheat | 1 | 1 | 1 | 1 | 1 | 1 | 1 | 2 | 1 | 1 | 2 | 3 | 3 | 3 | 3 | 3 | 1 | 1 | 1 | 1 | 1 | 1 | 1 | 1 | 1 | 1 | 1 | 1 |
| (part 2) | | | | | | | | | | | | | | | | | | | | | | | | | | | | |
| dead nettle | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 |
| amaranth | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 |
| winter rape-seed | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 |
| redshank | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 |
| corn poppy | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 |
| bristle grass | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 |
| finger grass | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 |
| sesbania spp. | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 |
| ipomoea spp. | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 |
| soybean | 1 | 1 | 1 | 1 | 1 | 1 | 1 | 1 | 1 | 1 | 1 | 1 | 2 | 3 | 3 | 1 | 1 | 3 | 4 | 2 | 2 | 3 | 3 | 2 | 2 | 3 | 3 | |
| cotton | 1 | 2 | 3 | 3 | 1 | 3 | 3 | 3 | 1 | 1 | 2 | 3 | 3 | 4 | 4 | 4 | 3 | 3 | 4 | 4 | 3 | 3 | 4 | 4 | 3 | 4 | 4 | 5 |

TABLE 3b-continued

| | Herbicidal action of the compounds of the invention in application amounts of 4, 3, 2 and 1 kg active substance/ha. Application after the sprouting of the plants | | | | | | | | | | | | | | | | | | | | | | | | | | | |
|---|---|---|---|---|---|---|---|---|---|---|---|---|---|---|---|---|---|---|---|---|---|---|---|---|---|---|---|---|
| Test Plants | Example 1 | | | | Example 2 | | | | Example 3 | | | | Example 4 | | | | Example 8 | | | | Example 9 | | | | Example 17 | | | |
| kg/ha | 4 | 3 | 2 | 1 | 4 | 3 | 2 | 1 | 4 | 3 | 2 | 1 | 4 | 3 | 2 | 1 | 4 | 3 | 2 | 1 | 4 | 3 | 2 | 1 | 4 | 3 | 2 | 1 |
| rice | 3 | 4 | 4 | 5 | 4 | 4 | 4 | 5 | 4 | 4 | 4 | 5 | 5 | 5 | 5 | 5 | 5 | 5 | 5 | 5 | 5 | 5 | 5 | 5 | 5 | 5 | 5 | 5 |
| corn | 1 | 1 | 3 | 3 | 4 | 4 | 4 | 4 | 4 | 4 | 4 | 5 | 4 | 4 | 4 | 4 | 3 | 4 | 4 | 4 | 4 | 4 | 4 | 5 | 4 | 4 | 5 | 5 |

The use of the compounds of the invention as soil herbicides in grain cultures has another advantage in addition to the specific activity against noxious grasses. In contrast to most of the previously known soil herbicides, the present compounds exhibit an especially broad spectrum of activity against dicotyledonous weeds encompassed with grain, and have very good activity against slender foxtail and many dicotyledonous weeds, in general.

Tables 3a and 3b show the good selectivity of the compounds of the invention in a few other important cultures (e.g., cotton) both in the pre-emergence and in the post-emergence periods.

C. Greenhouse Test Series with 0.5, 0.25 and 0.125 kg/ha

On account of the great herbicidal activity of the present compounds, several were tested, additionally, in even smaller application amounts (0.5, 0.25 and 0.125 kg active substance/ha and compared with two comparison means from the group of s-triazines.

Table 4 illustrates that the present compounds are superior to the reference compounds, Atrazine and Terbutryn, in herbicidal activity in significant ways. For example, the present compounds show superior activity against slender foxtail, corn grass, wild oats, chickweed, dead nettle and display a superior culture compatability in grain, for example.

grain, especially in barley and in wheat is achieved, particularly in the pre-emergence application.

Moreover, the products of the invention exhibit superior activity against panic grass types which are known to be noxious grasses in a few important cultures such as cotton and soybeans. In contrast to Atrazine, the present compounds are selective in cotton and soybeans.

Reference compound Terbutryn, 6-methylthio-2-ethyl amino-4-tert.butyl-amino-1,3,5-triazine, is selective in grains such as barley and wheat, but its activity against noxious grasses occurring in grain, such as slender foxtail or corn grass, is distinctly less than the compounds of the present invention. Moreover, neither Atrazine nor Terbutryn exhibits the selectivity in winter rape-seed which is exhibited by several of the present compounds, which were tested using lesser amounts.

Having now fully described this invention, it will be apparent to one of ordinary skill in the art that many changes and modifications can be made thereto without departing from the spirit or scope of the invention as set forth herein.

What is claimed as new and desired to be secured by Letters Patent of the United States is:

1. A herbicidal compound having the formula:

TABLE 4

| | | Herbicidal action of the compounds of the invention in application amounts of 0.5, 0.25 and 0.125 kg/ha before (VA) and after (NA) the sprouting of the test plants | | | | | | | | | | | | | | | | | |
|---|---|---|---|---|---|---|---|---|---|---|---|---|---|---|---|---|---|---|---|
| Compound | kg active subst./ha | slender foxtail | | corn grass | | barnyard grass | | corn | | chickweed | | camomile | | barley | | wheat | | winter rapeseed | |
| | | VA | NA | VA | NA | VA | NA | VA | NA | VA | NA | VA | NA | VA | NA | VA | NA | VA | NA |
| 1 | 0.5 | 1 | 1 | 1 | 1 | 1 | 1 | 3 | 3 | 1 | 1 | 1 | 1 | 4 | 1 | 4 | 1 | 5 | 1 |
| | 0.25 | 1 | 1 | 1 | 1 | 2 | 1 | 5 | 3 | 1 | 1 | 1 | 1 | 4 | 1 | 4 | 1 | 5 | 2 |
| | 0.125 | 2 | 1 | 2 | 1 | 3 | 2 | 5 | 5 | 3 | 1 | 1 | 1 | 5 | 2 | 5 | 2 | 5 | 2 |
| 2 | 0.5 | 1 | 1 | 1 | 1 | 1 | 1 | 5 | 5 | 1 | 1 | 1 | 1 | 4 | 1 | 4 | 1 | 4 | 1 |
| | 0.25 | 1 | 1 | 1 | 2 | 3 | 1 | 5 | 5 | 1 | 1 | 1 | 1 | 5 | 2 | 5 | 2 | 5 | 1 |
| | 0.125 | 2 | 1 | 3 | 3 | 5 | 1 | 5 | 5 | 3 | 1 | 1 | 1 | 5 | 2 | 5 | 2 | 5 | 1 |
| 3 | 0.5 | 1 | 1 | 1 | 1 | 2 | 1 | 5 | 5 | 1 | 1 | 1 | 1 | 5 | 3 | 5 | 3 | 5 | 1 |
| | 0.25 | 2 | 1 | 2 | 1 | 4 | 1 | 5 | 5 | 1 | 1 | 1 | 1 | 5 | 3 | 5 | 3 | 5 | 1 |
| | 0.125 | 3 | 1 | 4 | 2 | 5 | 3 | 5 | 5 | 3 | 1 | 1 | 1 | 5 | 5 | 5 | 3 | 5 | 2 |
| 4 | 0.5 | 1 | 1 | 1 | 1 | 1 | 1 | 5 | 5 | 1 | 1 | 1 | 1 | 5 | 3 | 5 | 3 | 4 | 1 |
| | 0.25 | 1 | 1 | 2 | 1 | 3 | 1 | 5 | 5 | 3 | 1 | 1 | 1 | 5 | 3 | 5 | 3 | 5 | 1 |
| | 0.125 | 2 | 1 | 3 | 2 | 4 | 2 | 5 | 5 | 4 | 1 | 1 | 1 | 5 | 4 | 5 | 5 | 5 | 2 |
| 17 | 0.5 | 2 | 1 | 1 | 1 | 4 | 1 | 5 | 5 | 1 | 1 | 1 | 1 | 5 | 4 | 5 | 3 | 5 | 1 |
| | 0.25 | 2 | 1 | 2 | 2 | 4 | 2 | 5 | 5 | 2 | 1 | 1 | 1 | 5 | 4 | 5 | 3 | 5 | 1 |
| | 0.125 | 2 | 1 | 3 | 3 | 5 | 3 | 5 | 5 | 4 | 1 | 1 | 1 | 5 | 4 | 5 | 4 | 5 | 1 |
| Atrazine | 0.5 | 1 | 1 | 1 | 1 | 2 | 1 | 5 | 5 | 1 | 1 | 1 | 1 | 1 | 1 | 1 | 1 | 3 | 1 |
| | 0.25 | 2 | 1 | 1 | 2 | 4 | 2 | 5 | 5 | 1 | 1 | 1 | 1 | 2 | 1 | 1 | 1 | 3 | 1 |
| | 0.125 | 2 | 1 | 1 | 3 | 4 | 3 | 5 | 5 | 1 | 2 | 1 | 1 | 3 | 2 | 2 | 2 | 3 | 1 |
| Terbutryn | 0.5 | 2 | 1 | 1 | 1 | 4 | 1 | 3 | 3 | 1 | 1 | 1 | 1 | 4 | 1 | 4 | 1 | 3 | 1 |
| | 0.25 | 2 | 1 | 2 | 2 | 4 | 1 | 4 | 3 | 1 | 1 | 1 | 1 | 4 | 1 | 4 | 1 | 3 | 1 |
| | 0.125 | 3 | 1 | 4 | 3 | 5 | 1 | 5 | 5 | 3 | 1 | 1 | 1 | 4 | 2 | 4 | 1 | 5 | 1 |

Also, in lower concentrations there is a selectivity in winter rape-seed in the pre-emergence period with effective activity against weeds and noxious grasses.

The compounds of the invention achieve or exceed the herbicidal activity of Atrazine against slender foxtail, corn grass, wild oats, chickweed, camomile and dead nettle. In contrast to Atrazine a superior activity in

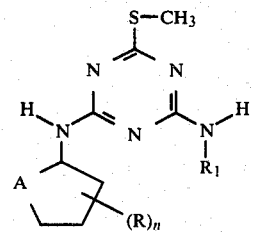

where R₁ is a straight-chained or a branched-chain alkyl, alkoxy or alkylol radical having less than a total of 15 oxygen and carbon atoms combined or a hydrogen atom; (R) is a lower alkyl group; A is —CH₂— or —CH₂CH₂—; with the proviso that n is 3, when A is —CH₂—, and n is 3–6, when A is —CH₂CH₂—; and wherein the substituents (R) on the cycloalkyl ring are identical to or different from each other.

2. The herbicidal compound according to claim 1, selected from the group consisting of 2,2,4- or 2,4,4-trimethylcyclopentylamino-4-amino-6-methylthio-s-triazine, 2,2,4- or 2,4,4-trimethylcyclopentylamino-4-methylamino-6-methylthio-s-triazine, 2,2,4- or 2,4,4-trimethylcyclopentylamino-4-ethylamino-6-methylthio-s-triazine, 2,2,4- or 2,4,4-trimethylcyclopentylamino-4-isopropylamino-6-methylthio-s-triazine, 2,2,4- or 2,4,4-trimethylcyclopentylamino-4-propylamino-6-methylthio-s-triazine, 2,2,4- or 2,4,4-trimethylcyclopentylamino-4-tert.butylamino-6-methylthio-s-triazine, 2,2,4- or 2,4,4-trimethylcyclopentylamino-4-2'methoxy-ethylamino-6-methylthio-s-triazine, 2,2,4- or 2,4,4-trimethylcyclopentylamino-4-3'methoxypropylamino-6-methylthio-s-triazine, 2,2,4- or 2,4,4-trimethylcyclopentylamino-4-3'ethoxy-propylamino-6-methylthio-s-triazine, 2,2,4- or 2,4,4-trimethylcyclopentylamino-4-3'butoxy-propylamino-6-methylthio-s-triazine, 2,2,4- or 2,4,4-trimethylcyclopentylamino-4-3'hexoxy-propylamino-6-methylthio-s-triazine, and 2,2,4- or 2,4,4-trimethylcyclopentylamino-4-3'isopropoxy-propylamino-6-methylthio-s-triazine.

3. The herbicidal compound of claim 1, which is selected from the group consisting of 3,3,5-trimethylcyclohexylamino-4-amino-6-methylthio-s-triazine, 3,3,5-trimethylcyclohexylamino-4-methylamino-6-methylthio-s-triazine, 3,3,5-trimethylcyclohexylamino-4-ethylamino-6-methylthio-s-triazine, 3,3,5-trimethylcyclohexylamino-4-isopropylamino-6-methylthio-s-triazine, 3,3,5-trimethylcyclohexylamino-4-propylamino-6-methylthio-s-triazine, 3,3,5-trimethylcyclohexylamino-4-tert.butylamino-6-methylthio-s-triazine, 3,3,5-trimethylcyclohexylamino-4-2'methoxy-ethylamino-6-methylthio-s-triazine, 3,3,5-trimethylcyclohexylamino-4-3'methoxy-propylamino-6-methylthio-s-triazine, 3,3,5-trimethylcyclohexylamino-4-3'ethoxy-propylamino-6-methylthio-s-triazine, and 3,3,5-trimethylcyclohexylamino-4-3'-butoxy-propylamino-6-methylthio-s-triazine.

4. A method for selectively treating useful plant cultures against weeds and noxious grasses before sprouting of the seed, after sprouting of the seed, or before and after sprouting of the seed, which comprises applying to said plant cultures a herbicidally effective amount of one or more compounds having the formula:

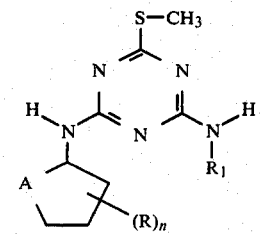

wherein R₁ is a straight-chain or a branched-chain alkyl, alkoxy or alkylol radical having less than a total of 15 oxygen and carbon atoms combined, or a hydrogen atom; (R) is a lower alkyl group; A is —CH₂— or —CH₂CH₂—; with the proviso that n is 3, when A is —CH₂—; and n is 3–6, when A is —CH₂CH₂—; and wherein the substituents (R) on the cycloalkyl ring are identical to or different from each other for any one compound; and an auxiliary agent selected from the group consisting of carrier agents, thinners, solvents, wetting agents, adhesion agents, dispersing agents and emulsifying agents.

5. The method of claim 4, wherein said one or more compounds are selected from the group consisting of 2,2,4- or 2,4,4-trimethylcyclopentylamino-4-amino-6-methylthio-s-triazine, 2,2,4- or 2,4,4-trimethylcyclopentylamino-4-methylamino-6-methylthio-s-triazine, 2,2,4- or 2,4,4-trimethylcyclopentylamino-4-ethylamino-6-methylthio-s-triazine, 2,2,4- or 2,4,4-trimethylcyclopentylamino-4-isopropylamino-6-methylthio-s-triazine, 2,2,4- or 2,4,4-trimethylcyclopentylamino-4-propylamino-6-methylthio-s-triazine, 2,2,4-or 2,4,4-trimethylcyclopentylamino-4-tert.butylamino-6-methylthio-s-triazine, 2,2,4- or 2,4,4-trimethylcyclopentylamino-4-2'methoxy-ethylamino-6-methylthio-s-triazine, 2,2,4- or 2,4,4-trimethylcyclopentylamino-4-3'methoxy-propylamino-6-methylthio-s-triazine, 2,2,4- or 2,4,4-trimethylcyclopentylamino-4-3'ethoxy-propylamino-6-methylthio-s-triazine, 2,2,4- or 2,4,4-trimethylcyclopentylamino-4-3'butoxy-propylamino-6-methylthio-s-triazine, 2,2,4- or 2,4,4-trimethylcyclopentylamino-4-3'hexoxy-propylamino-6-methylthio-s-triazine, and 2,2,4- or 2,4,4-trimethylcyclopentylamino-4-3'isopropoxy-propylamino-6-methylthio-s-triazine.

6. The method of claim 4, wherein said one or more compounds are selected from the group consisting of 3,3,5-trimethylcyclohexylamino-4-amino-6-methylthio-s-triazine, 3,3,5-trimethylcyclohexylamino-4-methylamino-6-methylthio-s-triazine, 3,3,5-trimethylcyclohexylamino-4-ethylamino-6-methylthio-s-triazine, 3,3,5-trimethylcyclohexylamino-4-isopropyl amino-6-methylthio-s-triazine, 3,3,5-trimethylcyclohexylamino-4-propylamino-6-methylthio-s-triazine, 3,3,5-trimethylcyclohexylamino-4-tert.butyl amino-6-methylthio-s-triazine, 3,3,5-trimethylcyclohexylamino-4-2'methoxy-ethylamino-6-methylthio-s-triazine, 3,3,5-trimethylcyclohexylamino-4-3'methoxy-propylamino-6-methylthio-s-triazine, 3,3,5-trimethylcyclohexylamino-4-3'ethoxy-propylamino-6-methylthio-s-triazine, and 3,3,5-trimethylcyclohexylamino-4-3'butoxy-propylamino-6-methylthio-s-triazine.

7. A herbicidal composition for the selective treatment of useful plant cultures having a broad spectrum of activity against weeds and noxious grasses before sprouting of the seed, and after sprouting of the seed, or before and after sprouting of the seed, which comprises one or more compounds having the formula:

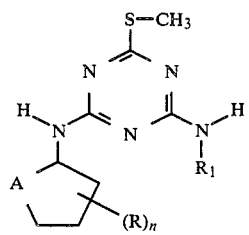

wherein $R_1$ is a straight-chain or a branched-chain alkyl, alkoxy or alkylol radical having less than a total of 15 oxygen and carbon atoms combined, or a hydrogen atom; (R) is a lower alkyl group; A is —CH$_2$— or —CH$_2$CH$_2$—; with the proviso that n is 3, when A is —CH$_2$—, and n is 3–6, when A is —CH$_2$CH$_2$—, wherein the substituents (R) on the cycloalkyl ring are identical to or different from each other for any single compound; and an auxiliary agent selected from the group consisting of carrier agents, thinners, solvents, wetting agents, adhesion agents, dispersing agents and emulsifying agents.

8. The herbicidal composition of claim 7, wherein said one or more compounds are selected from the group consisting of 2,2,4- or 2,4,4-trimethylcyclopentylamino-4-amino-6-methylthio-s-triazine, 2-2,4- or 2,4,4-trimethylcyclopentylamino-4-methylamino-6-methylthio-s-triazine, 2,2,4- or 2,4,4-trimethylcyclopentylamino-4-ethylamino-6-methylthio-s-triazine, 2,2,4- or 2,4,4-trimethylcyclopentylamino-4-isopropylamino-6-methylthio-s-triazine, 2,2,4- or 2,4,4-trimethylcyclopentylamino-4-propylamino-6-methylthio-s-triazine, 2,2,4- or 2,4,4-trimethylcyclopentylamino-4-tert.butyl amino-6-methylthio-s-triazine, 2,2,4- or 2,4,4-trimethylcyclopentylamino-4-2'methoxy-ethylamino-6-methylthio-s-triazine, 2,2,4- or 2,4,4-trimethylcyclopentylamino-4-340 methoxy-propylamino-6-methylthio-s-triazine, 2,2,4- or 2,4,4-trimethylcyclopentylamino-4-3'ethoxy-propylamino-6-methylthio-s-triazine, 2,2,4- or 2,4,4-trimethylcyclopentylamino-4-3'butoxy-propylamino-6-methylthio-s-triazine, 2,2,4- or 2,4,4-trimethylcyclopentylamino-4-3'hexoxy-propylamino-6-methylthio-s-triazine, and 2,2,4- or 2,4,4-trimethylcyclopentylamino-4-3'isopropoxy-propylamino-6-methylthio-s-triazine.

9. The herbicidal composition of claim 7, wherein said one or more compounds are selected from the group consisting of 3,3,5-trimethylcyclohexylamino-4-amino-6-methylthio-s-triazine, 3,3,5-trimethylcyclohexylamino-4-methylamino-6-methylthio-s-triazine, 3,3,5-trimethylcyclohexylamino-4-ethylamino-6-methylthio-s-triazine, 3,3,5-trimethylcyclohexylamino-4-isopropylamino-6-methylthio-s-triazine, 3,3,5-trimethylcyclohexylamino-4-propylamino-6-methylthio-s-triazine, 3,3,5-trimethylcyclohexylamino-4-tert.butyl amino-6-methylthio-s-triazine, 3,3,5-trimethylcyclohexylamino-4-2'methoxy-ethylamino-6-methylthio-s-triazine, 3,3,5-trimethylcyclohexylamino-4-3'methoxy-propylamino-6-methylthio-s-triazine, 3,3,5-trimethylcyclohexylamino-4-3'ethoxy-propylamino-6-methylthio-s-triazine, and 3,3,5-trimethylcyclohexylamino-4-3'butoxy-propylamino-6-methylthio-s-triazine.

* * * * *